United States Patent [19]
Boettger

[11] Patent Number: 5,827,244
[45] Date of Patent: *Oct. 27, 1998

[54] INTRAVENOUS INFUSION SYSTEM

[75] Inventor: Conrad H. Boettger, Hesston, Kans.

[73] Assignee: Via Christi Research Inc., Wichita, Kans.

[ * ] Notice: This patent issued on a continued prosecution application filed under 37 CFR 1.53(d), and is subject to the twenty year patent term provisions of 35 U.S.C. 154(a)(2).

[21] Appl. No.: 701,836

[22] Filed: Aug. 23, 1996

Related U.S. Application Data

[62] Division of Ser. No. 475,373, Jun. 7, 1995, which is a continuation of Ser. No. 67,394, May 25, 1993, Pat. No. 5,464,399, which is a continuation of Ser. No. 837,263, Feb. 18, 1992, abandoned.

[51] Int. Cl.$^6$ .................................................. A61M 25/00
[52] U.S. Cl. ............................................................ 604/283
[58] Field of Search ........................... 604/283, 240–243, 604/246–247, 284, 239, 80–81

[56] References Cited

U.S. PATENT DOCUMENTS

| | | |
|---|---|---|
| 3,831,629 | 8/1974 | Mackal et al. . |
| 4,311,137 | 1/1982 | Gerard . |
| 4,324,239 | 4/1982 | Gordon et al. . |
| 4,429,856 | 2/1984 | Jackson . |
| 4,535,820 | 8/1985 | Raines . |
| 4,636,204 | 1/1987 | Christopherson et al. . |
| 4,683,916 | 8/1987 | Raines . |
| 4,745,950 | 5/1988 | Mathieu . |
| 4,838,875 | 6/1989 | Somor . |
| 4,886,507 | 12/1989 | Patton et al. . |
| 5,127,904 | 7/1992 | Loo et al. ................................. 604/247 |
| 5,163,922 | 11/1992 | McElveen, Jr. et al. . |
| 5,171,234 | 12/1992 | Jepson et al. . |
| 5,188,620 | 2/1993 | Jepson et al. ............................ 604/283 |
| 5,190,534 | 3/1993 | Kendell . |
| 5,203,771 | 4/1993 | Melker et al. ........................... 604/283 |
| 5,464,399 | 11/1995 | Boettger . |

FOREIGN PATENT DOCUMENTS 0546004  3/1958  Italy .

OTHER PUBLICATIONS

Brochure from Burron Medical Inc., Bethlehem, PA, entitled "Remove the Risk . . . by removing the needle" (4 pages).
Brochure from Baxter Healthcare Corporation entitled "Announcing a major breakthrough — that won't" (5 pages).
Brochure from Tri–State Hospital Supply Corporation, Howell, Michigan entitled "Centurion, The Kleen–Needle System for Risk–Free Catheter Management" dated Jun. 1990 (2 pages).
Halkey–Roberts Product Information Sheet M–01, Jan. 1990 5M (1 page).
Halkey–Roberts Product Information Sheet M–02 entitled Luer Syringe Check Valves, dated Jan. 1960 5M(2 pages).
Becton–Dickinson Information Sheet B–D900110 entitled B–D Safety–Loc Syringe with built–in needlestick protection dated 1990 (2 pages).

*Primary Examiner*—Manuel Mendoz
*Attorney, Agent, or Firm*—Hovey,Williams, Timmons & Collins

[57] ABSTRACT

A quick-connect, needleless coupling assembly configured to shield its critical areas from contamination by environmental surfaces has a pair of interlocking, flow-through male and female components which may be used as part of a larger medicinal liquid therapy system. The male component has a generally rigid, blunt, open-ended cannula which is recessed with respect to a surrounding concentrically spaced collar so that the open end of the cannula is protected against contact from environmental surfaces which might otherwise contaminate the cannula. The female component has a socket which receives the male cannula to place the two components into liquid flow communication with one another. In the preferred form of the invention, the two components are threadably inter-locked with one another, the female component being provided with an internal depressible valve stem which is operated by the rigid cannula when the components are threaded together, thereby opening an anti-back flow check valve within the female component.

6 Claims, 3 Drawing Sheets

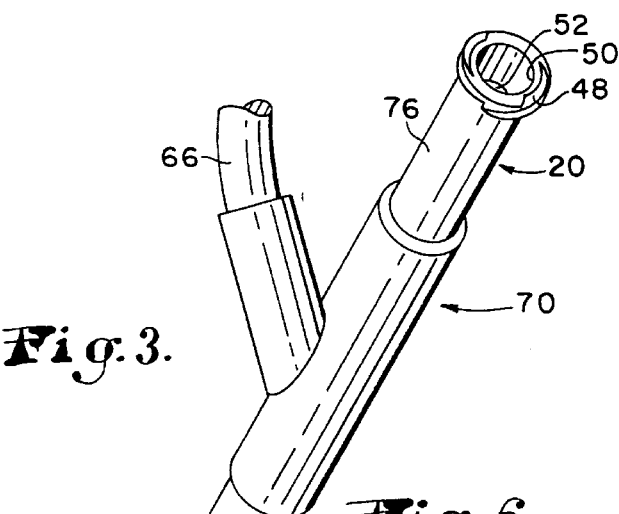
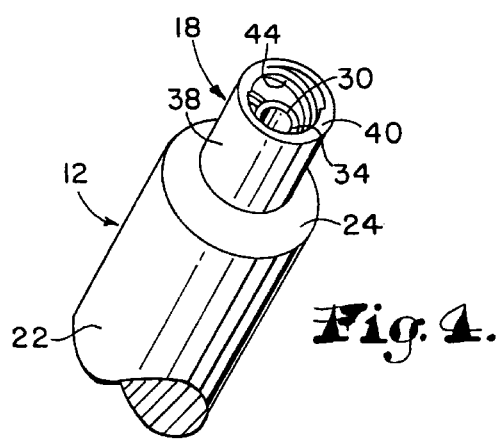
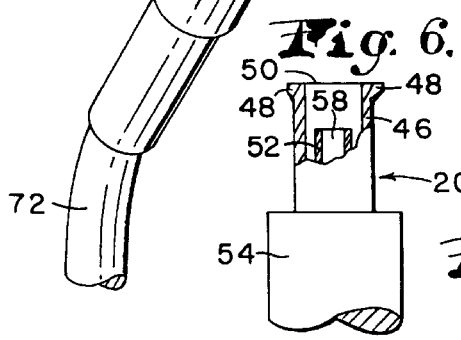
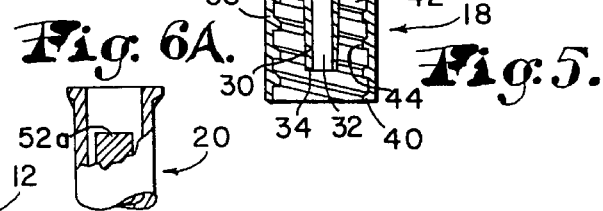
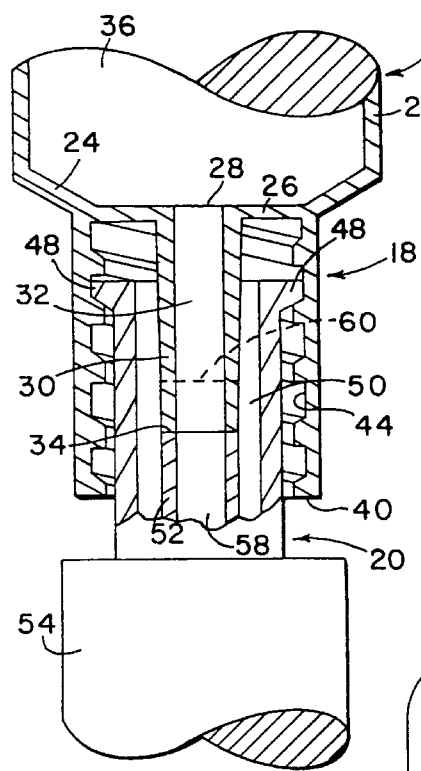
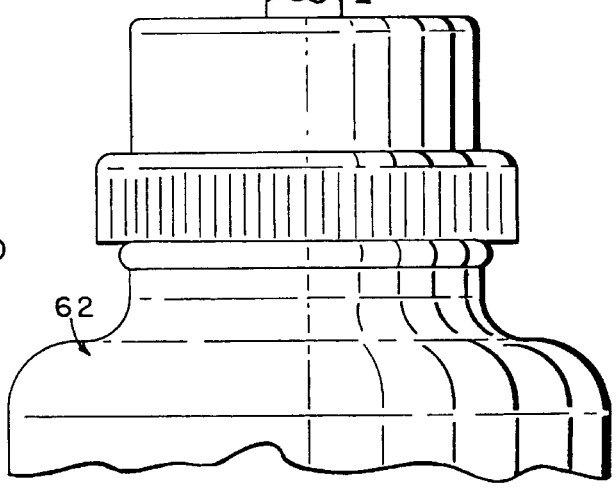

INTRAVENOUS INFUSION SYSTEM

This is a division of application Ser. No. 08/475,373, filed Jun. 7, 1995 which is a continuation of prior application Ser. No. 08/067,394, filed May 25, 1993 (now U.S. Pat. No. 5,464,399), which is a continuation of prior application Ser. No. 837,263, filed Feb. 18, 1992 (now abandoned).

TECHNICAL FIELD

The present invention relates generally to systems for administering fluids such as medicinal liquids to patients in hospitals, doctors offices, home settings, clinics and emergency field trauma situations, and, more particularly, relates to improvements in flow-through, quick disconnect and connect couplings used in association with tubings, syringes, vials, bags, and other such equipment commonly associated with medicinal liquid therapies.

BACKGROUND

In the administration of medicinal liquids using intravenous techniques, it is important and critical to avoid contamination of otherwise sterile devices and to avoid the spread of infections of various kinds through accidental needle sticks. Not only are the patients at risk throughout the administration of intravenous therapy, but also the care giver and other individuals within the health care environment are exposed to considerable risks if appropriate protective measures are not taken at all potential trouble spots within the procedure. Even activities as far removed from the immediate patient site as the disposal of discarded, used equipment can present significant danger, such as through the inadvertent puncture of the worker by blood-contaminated needles projecting through trash bags and the like.

As a consequence of these types of risks, there has been a trend in the health care industry toward the reduction and elimination of steel needles in connection with intravenous therapy. For example, instead of using a steel needle to penetrate a port of a catheter which has been installed at an appropriate access point on a patient's body, some currently available products utilize a variety of plastic couplings and valves for the purpose of communicating the catheter with the syringe, tubing, or other medical appliance administered by the practitioner. While such devices are helpful in the sense they reduce the risks associated with needle sticks, unfortunately, in many instances, there is still a significant potential for contamination due to exposed critical surfaces.

Accordingly, one important object of the present invention is to provide a quick connect coupling system or assembly which is particularly, although not exclusively, usable in connection with needleless medicinal liquid delivery systems and which lowers the risks of contamination associated with current IV therapies, including those which contemplate the use of steel needles or unprotected plastic cannulas for accessing the system. In this respect, it is an important object of the invention to provide male and female components of the assembly which are quickly and easily connectable and disconnectable from one another while the projecting, blunt cannula of the male component which establishes liquid flow communication with the female component is shielded from exposure to environmental elements before, during, and after interconnection with the female component, thereby helping to avoid any contact with contaminated surfaces and objects.

Another important object of the present invention is to provide a quick connect and disconnect coupling system which is readily adaptable for use on a wide variety of system components, such as, for example, syringes, check valves, flexible tubings and flow lines, vials of both the single dosage and multi-dosage type, injection ports, access sites associated with a variety of components, and liquid supply bags and other containers for medicinal fluids. When the invention is used in connection with syringes, for example, it is contemplated that the male component with its recessed blunt cannula will be disposed on and form an integral part of the syringe body, while the female component with its receiving socket for the recessed cannula is disposed on the injection port, back flow check valve, or other major part of the system. Instead of using a puncturable membrane on drug vials and injection ports of flexible tubings, the present invention contemplates that such equipment will be provided with the female component and back flow check valve of the present invention so that the syringe or other appliance having the male component of the assembly integrated therewith is readily usable with the modified vial or injection port.

In carrying out the principles of the present invention, it is contemplated that the recessed, blunt cannula of the male component is protectively surrounded by an annular collar having an axially endmost extremity that projects outwardly beyond the open end of the cannula. In this manner, once a protective sheath or wrapper has been removed from the syringe or other appliance to be utilized by the practitioner, the protective collar becomes that portion of the appliance which is exposed to environmental surfaces and human contact. Consequently, the critical open end of the cannula itself remains in a sheltered and guarded position throughout the manipulation which is always necessary to access the system for administering the medicinal therapy.

In its preferred form, the cannula of the male component is sufficiently rigid as to serve as a means for depressing the valve stem of a normally closed valve which may be incorporated into the female component of the assembly whereby to open the valve. The valve stem may be a solid stem which, when depressed, allows fluid flow around its external surfaces due to a change in position of such surfaces relative to the internal portions of the valve chamber. On the other hand, the stem may be tubular such that liquid flow is directly through the cannula and into the tubular open end of the valve stem when the components of the coupling assembly have been connected together. Preferably, such coupling is accomplished by intermeshing threads on the two components. Furthermore, it is preferred that the male cannula have a luer taper in which the diameter of the cannula becomes progressively reduced as the open blunt end thereof is approached, thereby adapting the cannula to be press-fit into matingly luer-tapered female sockets associated with other components than those having a depressible valve stem.

The male component of the present invention may be attached directly to current design female-ended catheters, ports, and cannulas not provided with integral back-flow check valve systems.

BRIEF DESCRIPTION OF THE DRAWINGS

FIG. 3 is an enlarged, fragmentary, perspective view of one of the Y-type injection sites with an internal anti-backflow check valve in the supply tubing of FIG. 2;

FIG. 4 is an enlarged, fragmentary, perspective view of the end of a syringe provided with the male component of the present invention;

FIG. 5 is a fragmentary, longitudinal, cross-sectional view of the male component of the assembly on the syringe of FIG. 4;

FIG. 6 is a fragmentary, elevational view of the female component of the present invention formed upon an appliance such as the receiving end of the injection port of FIG. 3, the protective circumscribing wall of the female component being partially broken away to reveal internal details including a tubular, depressible valve stem of an anti-backflow check valve associated with the female component;

FIG. 6a is a fragmentary, elevational view of the female component of the present invention formed upon the receiving end of a second type of injection port in which the associated anti-backflow check valve has a solid, depressible valve stem;

FIG. 7 is an enlarged, fragmentary view of the coupling assembly with portions broken away to reveal details of construction and illustrating the male and female components of the coupling firmly connected together in liquid flow communication with one another, the female component being integrated with a back flow check valve having a depressible, tubular stem which has been depressed from its phantom line position in FIG. 8 to its solid line, open position;

FIG. 8 is a fragmentary, elevational view on a reduced scale of the quick connect coupling of the present invention used in connection with a drug vial, rigid liquid supply container or the like in which the two major components of the assembly are intercoupled as illustrated in FIG. 7;

DETAILED DESCRIPTION

Figure 1:
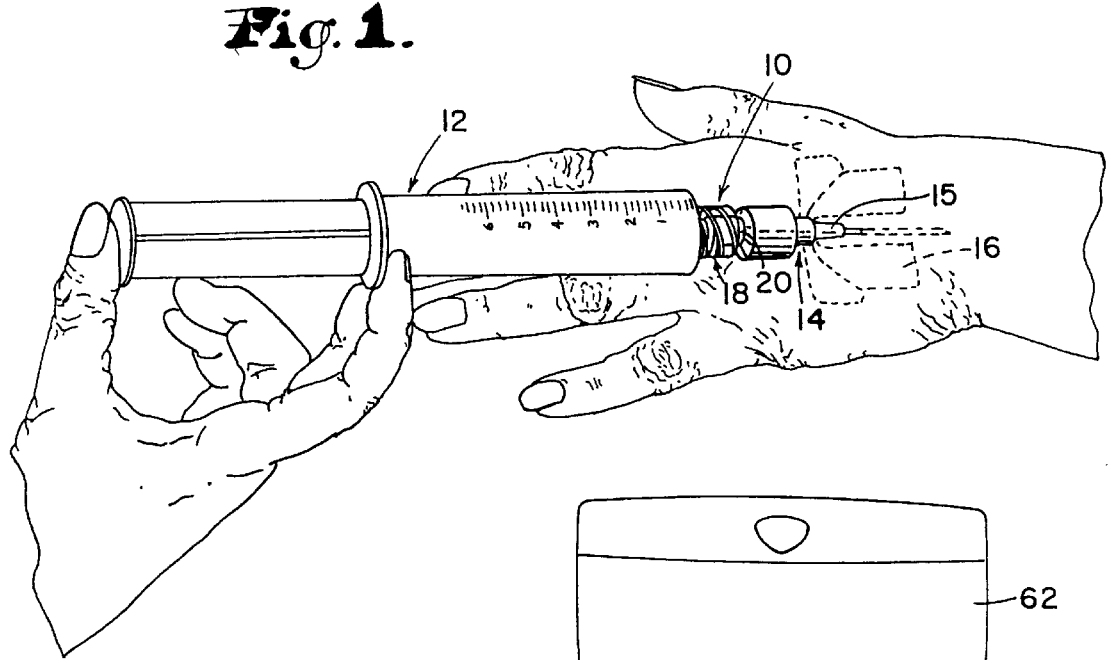
FIG. 1 is a perspective illustration of a system suitable for the intermittent administration of a medicinal liquid to a human or veterinary patient utilizing a syringe, straight injection port and catheter provided with a quick-attach, needleless coupling in accordance with the principles of the present invention.

The quick-attach coupling assembly of the present invention may be utilized in connection with a number of appliances or devices used by the health care practitioner. In FIG. 1, for example, the coupling assembly 10 is shown in use with a hypodermic syringe 12 and a straight injection port 14 that connects to an intravenous catheter 15 of the type which is anchored on the skin of the patient by tape 16 or other suitable means so that the intravenous catheter remains stabilized within the vein of the patient even during changes of the syringe 12.

As particularly shown in FIGS. 4, 5, 6 and 6a, the coupling assembly 10 of the present invention broadly comprises a pair of interconnectable components 18 and 20 which may be incorporated into and made integral parts of various components of a medicinal liquid supply system. In FIGS. 4 and 5, it will be appreciated that the male component 18 of the assembly 10 is incorporated into the discharge end of the syringe 12, the main cylindrical body of the syringe 12 being denoted by the numeral 22 in FIGS. 4 and 5. The cylindrical body 22 has an inclined, annular end wall 24 that tapers toward the male component 18. A transverse, internal end wall 26 of the body 22 has an orifice 28 disposed on the axial centerline of the body 22.

The male coupling component 18 is fixedly secured to the transverse end wall 28 such as by integral molding therewith and includes an essentially rigid cannula 30 having a central bore 32 registered with the orifice 28 and an open, blunt end 34. The open blunt end 34 of the cannula 32 has the effect of establishing a liquid flow passage through the component 18 and the body 22 of the syringe 12 defined by the bore 32 and the interior chamber 36 within the hollow body 22. In its preferred form, the cannula 30 is disposed in concentric relationship with the body 22 on the longitudinal axis of the latter. Furthermore, in its preferred form, the cannula 30 is provided with a luer taper, progressively reducing in diameter as the blunt end 34 is approached from the transverse end wall 26.

The male component 18 also includes an elongated, annular collar 38 which circumscribes the cannula 30 in radially spaced relation therewith and is fixedly joined to the cylindrical body 22 at the intersection of the inclined end wall 24 with the transverse end wall 26. The collar 38 is concentric with the cannula 30 and is substantially longer than the latter so as to present an axially endmost extremity 40 that is located outwardly beyond the blunt end 34 of the cannula 30. Thus, the end 34 of cannula 30 is substantially recessed with respect to the end extremity 40 and is protectively shielded by the latter.

An annular space 42 is defined within the collar 38 by virtue of the large internal diameter of the collar 38 compared to the outside diameter of the cannula 30, such space 42 being used to receive a portion of the female component 20 as will hereinafter be made clear. A series of internal threads 44 are formed on the interior surface of the collar 38, extending from the endmost extremity 40 to the transverse end wall 26 for use in releasably connecting the female component 20 with the male component 18.

The female component 20 has an elongated, annular outer wall 46 that is of slightly smaller outside diameter than the inside diameter of the collar 38. Threads 48 at the axially outermost end of the wall 46 are configured to mate with the internal threads 44 of the male component 18 such that the threads 44 and 48 serve as structure for removably connecting the components 18 and 20 together when the components are assembled as illustrated in FIG. 7. The annular wall 46 defines an open ended, elongated receiving socket 50 having a diameter large enough to accept the cannula 30 of the male component 18 when the components 18 and 20 are connected together. The socket 50 may be communicated directly with an internal path (not shown) for liquid flow through the component 20 or, or in its preferred form, the component 20 may be incorporated into an anti-back flow check valve of well-known design. One such check valve is disclosed in U.S. Pat. No. 4,535,820 in the name of Raines. Such check valve is commercially available from Burron Medical, Inc., of Bethlehem, Pa., and is marketed as a component of the company's "Safsite Extension Set", commonly being referred to as a "reflux valve". Such valve is also disclosed in a publicly available sales brochure titled "Remove the Risk . . . By Removing the Needle" published by Burron Medical, Inc. Such sales brochure and said U.S. Pat. No. 4,535,820 are hereby incorporated by reference into the present disclosure as need be for a full and complete understanding of the present invention.

In the event that the female component 20 is incorporated into a check valve of the above-described type, the socket 50, instead of being directly communicated with a liquid flow path through the component 20, receives a tubular, depressible valve stem 52 associated with a check valve housed within a main body 54 of the device. The valve stem 52 has a blunt open end 56 that has an internal path 58 leading away from the open end 56 to other portions of the valve. In the normally closed position of FIG. 6, the valve stem 56 maintains the valve (not shown) closed to preclude fluid flow through the main body 54 and the remainder of the system to which it is coupled, while when the stem 52 is depressed, the internal valve is forced open to allow fluid flow.

FIG. 6a illustrates a second preferred form of check valve with which the female component 20 may be associated. In this particular form, the depressible valve stem 52a is solid rather than tubular. When depressed, the stem 52a opens a fluid flow pathway around external rather than internal surfaces thereof. One such suitable solid stemmed valve is available from Halkey-Roberts, Inc., of St. Petersburg, Fla. Such valve is also disclosed in U.S. Pat. No. 3,831,629 to Mackal, et al., which is hereby incorporated by reference into this specification as need be for a full and complete understanding of the present invention.

FIG. 7 illustrates the manner in which the components 18 and 20 may be removably connected together when the male component 18 is part of a syringe such as the syringe 12 and the female component 20 is part of a reflux valve of the type above described in FIG. 6. It will be appreciated that when the components 18 and 20 are brought into axial alignment with the annular wall 46 of the female component 20 in registration with the annular space 42 of the male component 18, relative rotation of the two components while they are moved axially toward one another causes the threads 44 and 48 to matingly inter-engage and draw the female component 20 up into the male component 18. As relative rotation in the appropriate direction continues, the open end 34 of the rigid cannula 30 comes to bear against the similarly open end 56 of the valve stem 52 at the dotted line location indicated by the reference numeral 60. Continued relative rotation of the two parts causes the valve stem 52 to be depressed by the cannula 30, opening the internal valve within the body 54 and establishing liquid flow communication between the body 54 and the interior chamber 36 of the syringe 12. If a valve having the solid valve stem 52a of FIG. 6a is used rather than the tubular stem 52, the action will be similar to that described with respect to FIG. 7 but liquid leaving the cannula 30 will escape through a cross slot or the like in the depressed solid stem 52a and enter the socket 50 for movement through the valve externally of the stem 52a.

In order to disconnect the syringe 12 from the body 54, it is only necessary to relatively rotate the syringe 12 and the body 54 in the opposite direction from that utilized to secure the parts together, which causes the valve stem 52 to yieldably return to the dotted line position 60 and reestablish closure of the internal valve. A suitable closure cap (not shown) may be applied to the otherwise open end of the female component 20 after disconnection from the syringe 12. If desired, a likewise suitable closure may be provided for the male component 18 of the syringe 12.

FIG. 8 shows how the valve body 54 incorporating the female component 20 may be utilized in connection with a rigid liquid supply container or a drug vial 62, in lieu of a rubberized or plastisized membrane port such as currently commercially available. In either the single or multi-dose type, the vial 62 and its female component 20 must have a suitable anti-backflow valve or other type shut-off flow valve associated with it to prevent liquid flow and maintain content sterility during periods of non-use.

Figure 2:
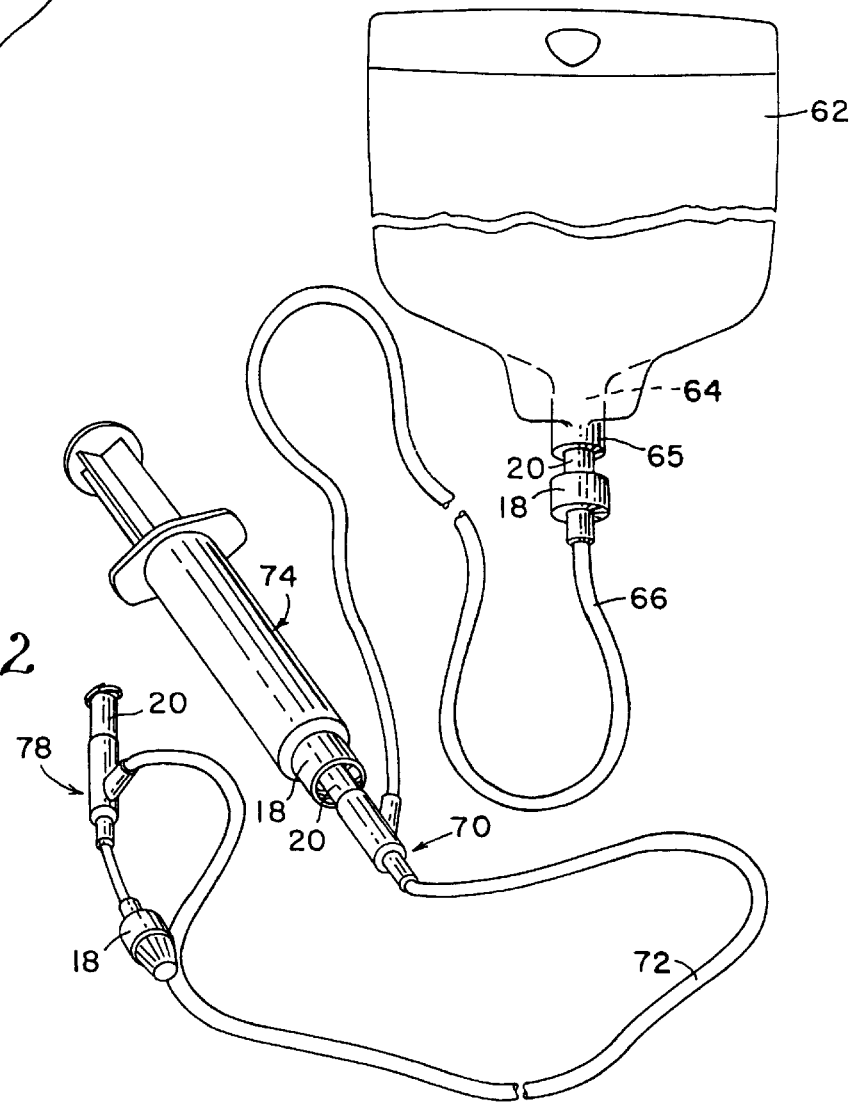
FIG. 2 is a perspective illustration of couplings of the present invention in use not only with a hypodermic syringe, but also with a flexible liquid tubing having multiple Y-type injection sites or ports and a flexible, variable volume liquid supply bag which is adapted to be connected with such flexible line.

FIGS. 2 and 3 show the male and female coupling components 18, 20 utilized in connection with a flexible dispensing bag and supply tubing system. In this contemplated manner of use, the flexible supply bag 62 contains a medicinal liquid which will be delivered to an injection site or other location such as represented by the intravenous catheter 15 in FIG. 1. The bag 62 has been adapted with a single filling and discharge port 64 equipped with the female component 20 of the quick coupling system provided with an integral anti-backflow valve 65 which is normally closed but opens upon interconnection of the components 18 and 20. The male coupling component 18 is fitted onto the uppermost end of the flexible tubular supply line 66.

The line 66 in turn leads to a Y-type access port broadly denoted by the numeral 70 (see, also, FIG. 3) which maintains communication between the line 66 and a second length of tubing or line 72, but which may be accessed by a syringe 74 or other similarly male ended supply line via the female end 20 of the access port 70 for the injection of additional medicinal liquids if desired. Having the female component 20 of the present invention on the access port 70 facilitates quick connect and disconnect of the syringe 74 or IV supply tubing which likewise incorporates the male component 18 of the present invention.

The line segment 72 at its end remote from the Y-type access port 70 may be provided with one or more additional Y-type access ports 78 which are of similar design to the access port 70 and which in their preferred form are provided with the female component 20 of the instant invention.

It will be appreciated that depending upon the particular type of intravenous system which is set up, it may be desirable to use a part or combination of parts which ultimately has two of the male components 18 at opposite ends thereof. For example, this would permit the free end of the Y-type access port 78 in FIG. 2 to be connected to a fitting or intermediate coupling having the male component 18 thereon, which would in turn be connected directly to the female component 20 associated with the intravenous catheter in FIG. 1. Likewise, in some situations it may be desirable to have a single component or a combination of components arranged in such a manner that opposite ends of the resulting assembly are both provided with a female connecting component 20.

Figure 14:
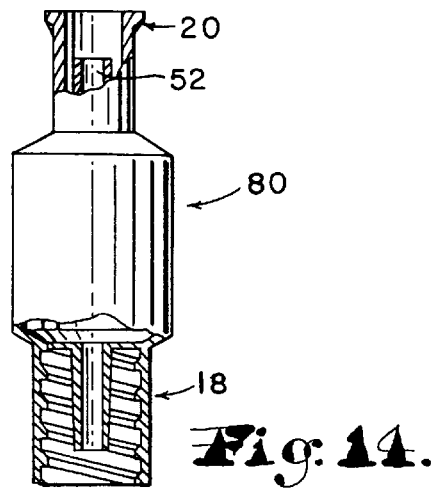
FIG. 14 is a largely elevational view of a straight injection port having male and female components in accordance with the present invention formed at its opposite ends and including an internal, anti-backflow check valve.

FIG. 14 shows a straight injection port 80 in which the male component 18 of the present invention is formed at one end and the female component 20 of the present invention is formed at the opposite end. The female component 20 chosen for illustration has the tubular, depressible valve stem 52 therein, although it will be appreciated that the solid valve stem 52a could alternatively be provided. The injection port 80 has an internal anti-backflow check valve of suitable design as previously discussed.

Figure 9:
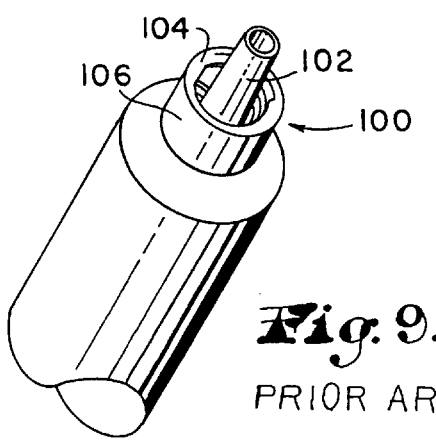
FIG. 9 is a fragmentary, perspective illustration of a prior art syringe having an exposed, unprotected and outwardly projecting male cannula.
Figure 10:
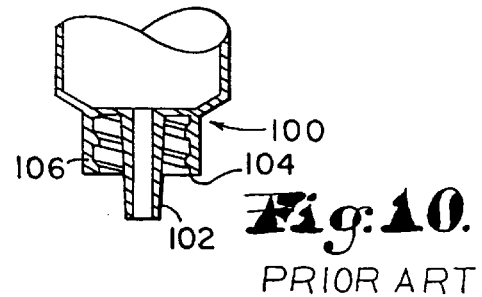
FIG. 10 is a fragmentary, longitudinal, cross-sectional view of the prior art syringe of FIG. 9.
Figure 13:
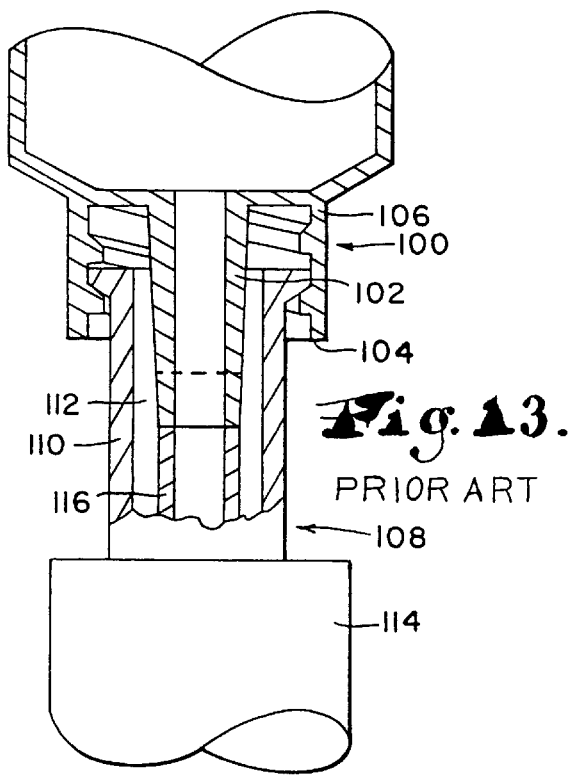
FIG. 13 is a fragmentary, elevational view with parts shown in cross-section of the prior art male and female components connected together and showing the female component integrated as part of a back flow check valve having a depressible, tubular valve stem.

FIGS. 9 through 13 are illustrations of prior art quick-attach coupling components. As illustrated in FIG. 9 and FIG. 10 in particular, the prior male coupling component 100 included a rigid, tubular cannula 102 which projected outwardly beyond the endmost extremity 104 of a annular collar 106 circumscribing the cannula 102 in spaced, concentric relationship therewith. Consequently, the cannula 102, once unsheathed from a protective wrapper or the like, was exposed to contamination by contact with environmental surfaces, including but not limited to the practitioner's own hands and fingers.

Figure 12:
FIG. 12 is a fragmentary, perspective view of the prior art female component of FIG. 11.
Figure 11:
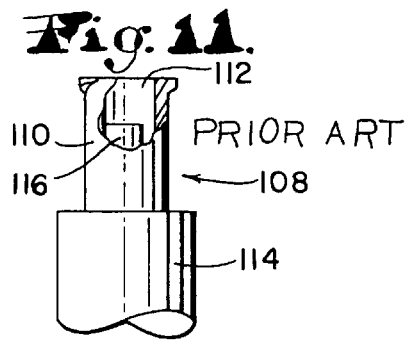
FIG. 11 is a fragmentary, elevational view of a prior art female coupling component, the exterior sidewall of the component being broken away to reveal internal details.

The female component 108 of the prior art as shown particularly in FIGS. 11 and 12, included an annular outer wall 110 defining an internal, cylindrical socket 112 for reception of the cannula 102 associated with the male component 100. The prior art female component 108 could also be integrated with a valve body 114 containing a suitable anti-back flow check valve actuated by a tubular, open ended, depressible valve stem 116 situated axially within the socket 112 in disposition for depressible actuation by the cannula 102 when the components 100 and 108 were coupled together in the manner illustrated in FIG. 13. Intermeshing threads 118 and 120 on the interior wall of the collar 106 and the exposed outermost end of the wall 110 of the female component 108 served as structure for holding the components 100 and 108 releasably connected together.

It is contemplated that the quick-connect coupling components of the present invention may be manufactured from a suitable plastic such as a polystyrene material. In this manner, the components are readily manufacturable at a relatively reasonable cost and can be treated as disposable components. They may also form a part of a completely needleless intravenous infusion system so that the risk of needle stick injuries, especially when the practitioners are in a hurry, can be almost completely eliminated.

It will be appreciated that current therapy techniques utilizing needles present a number of significant risks directly associated with the needles. If a sharpened needle is to be used to puncture a rubberized injection port, such port must first be cleansed with alcohol/betadine to ensure sterility prior to the puncture.

After unsheathing the needle, the needle must be maintained as a sterile device throughout puncturing of the port, the injection of the medication, and the subsequent removal of the needle from the port. Then, the needle must be safely discarded without contaminating anything in the environment.

Of course during discard of the needle-bearing syringes or the needles themselves, there is a likelihood that they will accidently puncture the care giver or ancillary staff responsible for carrying out their disposal. This is made all the more serious by the fact that once the needles have been used with the patient, they are contaminated with the body fluids of the patient and are therefore hazardous carriers of potentially lethal pathogens for all persons who may be accidentally punctured by them. Applying a protective cap or sheath to the needle after use and prior to disposal is desirable yet risky because the extra operation presents an extra opportunity for needle stick.

Furthermore, it is quite possible with needles and current plastic fluid access spikes to accidentally puncture the fluid volume devices such as bags or containers typically utilized to hold a medicinal liquid to be administered to a patient. When an erroneous puncture occurs, the entire fluid volume is contaminated. Moreover, a leak point is produced which potentially exposes the care giver and others to potentially toxic substances.

Even in prior systems having non-metal spikes and the like for puncturing sealing membranes or other structures, such puncturing devices are still exposed to contamination by environmental surfaces. Absolutely meticulous adherence to aseptic techniques throughout the puncturing and medicinal administration process must be ensured.

Accordingly, it should be apparent that the present invention provides a significant advancement in this art by eliminating serious risks inherent in present systems while maintaining user friendly components at a reasonable cost.

Although preferred forms of the invention have been described above, it is to be recognized that such disclosure is by way of illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventor hereby states his intent to rely on the Doctrine of Equivalents to determine and assess the reasonably fair scope of his invention as pertains to any apparatus not materially departing from but outside the liberal scope of the invention as set out in the following claims.

I claim:

1. A needleless IV infusion system comprising:

a flexible tubular supply line for use in delivering a primary liquid from a source of supply to a patient's vascular system;

a pair of needleless connectors at opposite ends of the line for joining the line with mating needleless components at the source of supply and proximal to the patient, respectively; and a multiplicity of needleless secondary access ports in the line for providing multiple, selectively usable, secondary sites of access to the patient's vascular system, each of said secondary access ports comprising:

a hollow body having a primary inlet fixedly joined to an upstream segment of the supply line, a primary outlet fixedly joined to a downstream segment of the supply line, and a secondary inlet communicating with said primary outlet;

a normally closed check valve associated with said secondary inlet for maintaining the secondary inlet closed unless intentionally opened by a device that becomes detachably secured to the body for the purpose of accessing the patient's vascular system through the secondary port; and releasable locking structure on the body at said secondary inlet for engagement with mating locking structure on the device to detachably secure the device to the body during access to the patient's vascular system through the secondary port, said locking structure on the body comprising a female luer lock end permanently secured to the body and including a generally cylindrical, annular wall having external threads disposed for meshing engagement with internal threads on the device to be attached to the female luer end, said check valve including a one-piece, resilient poppet yieldably biased into a closed position and having an actuating stem that projects axially into surrounded relationship with the wall of the female luer end for opening depression by the device attached to the secondary inlet.

2. A needleless IV infusion system as claimed in claim 1, said hollow body of each secondary port being generally Y-shaped, said primary outlet and one of said inlets being in axial alignment with one another, the other of said inlets being disposed at an oblique angle with respect to said primary outlet and said one inlet.

3. A needleless IV infusion system as claimed in claim 1, each of said connectors at opposite ends of the line having male luer lock structure associated therewith for mating engagement with female luer structure on needleless components selectively attachable to the connectors.

4. A needleless IV infusion system as claimed in claim 3, each of said connectors being configured to present a cannula having a blunt, open outer end and an annular, outer collar circumscribing said cannula in radially spaced relation therewith.

5. A needleless IV infusion system as claimed in claim 1; and a needleless, straight injection port detachably coupled with said connector at one end of the supply line, said straight injection port having a normally closed check valve therein which is opened when the straight injection port is joined to the line by the connector, said straight injection port comprising said component at the end of the line proximal to the patient.

6. A needleless IV infusion system as claimed in claim 1; and a bag comprising said source of supply of the liquid, said bag having a straight injection port that comprises said needleless component to which a connector of the system is joined, said straight injection port including a normally closed check valve which becomes opened when the line is joined to the bag by connecting the connector with the straight injection port.

* * * * *